(12) United States Patent
Ishikura et al.

(10) Patent No.: US 8,436,047 B2
(45) Date of Patent: May 7, 2013

(54) PREVENTIVE OR AMELIORATING AGENT FOR LIVER DISEASE INVOLVING HEPATOPATHY

(75) Inventors: Yoshiyuki Ishikura, Ibaraki (JP); Hiroshi Kawashima, Takatsuki (JP); Tomohito Hamazaki, Toyama (JP); Shiro Watanabe, Toyama (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1165 days.

(21) Appl. No.: 10/562,716

(22) PCT Filed: Jan. 19, 2005

(86) PCT No.: PCT/JP2005/000941
§ 371 (c)(1),
(2), (4) Date: Jan. 23, 2006

(87) PCT Pub. No.: WO2005/067914
PCT Pub. Date: Jul. 28, 2005

(65) Prior Publication Data
US 2006/0217442 A1    Sep. 28, 2006

(30) Foreign Application Priority Data
Jan. 20, 2004  (JP) ................................ 2004-012207

(51) Int. Cl.
*A61K 31/22* (2006.01)
*A61K 31/202* (2006.01)
*C12P 7/64* (2006.01)

(52) U.S. Cl.
USPC ........................... 514/547; 514/560; 435/134

(58) Field of Classification Search .................. 514/547, 514/560; 435/134
See application file for complete search history.

(56) References Cited

U.S. PATENT DOCUMENTS

| | | | |
|---|---|---|---|
| 4,432,906 A | 2/1984 | Cohen et al. | |
| 4,434,101 A | 2/1984 | Cohen et al. | |
| 4,681,896 A | 7/1987 | Horrobin | |
| 5,130,147 A | 7/1992 | Karu | |
| 5,260,336 A | 11/1993 | Forse et al. | |
| 5,320,846 A * | 6/1994 | Bistrian et al. ................ | 424/439 |
| 5,589,508 A | 12/1996 | Schlotzer et al. | |
| 5,981,588 A | 11/1999 | Akimoto et al. | |
| 2004/0171127 A1* | 9/2004 | Akimoto et al. .............. | 435/134 |

FOREIGN PATENT DOCUMENTS

| | | |
|---|---|---|
| CN | 1468060 A | 8/2007 |
| EP | 0260655 A2 | 3/1988 |
| EP | 0 535 939 A1 | 4/1993 |
| EP | 0635266 A1 | 1/1995 |
| EP | 0 704 211 A2 | 4/1996 |
| JP | 62195346 A | 8/1987 |
| JP | 63072648 A | 4/1988 |
| JP | 64019040 U | 1/1989 |
| JP | 64026532 U | 1/1989 |
| JP | 5-91888 | 4/1993 |
| JP | 6033087 A | 2/1994 |
| JP | 7-508720 | 9/1995 |
| JP | 8-53349 | 2/1996 |
| JP | 11 116473 A | 4/1999 |
| WO | 97/05863 | 2/1997 |
| WO | 99/48531 | 9/1999 |
| WO | 01/28555 A1 | 4/2001 |
| WO | 02-53892 | 2/2002 |
| WO | WO 02/11551 A2 | 2/2002 |
| WO | 03/004667 A1 | 1/2003 |

OTHER PUBLICATIONS

International Search Report of PCT/JP2005/000941, mailed May 31, 2005.
Hirabayashi et al., Inhibition of Metastatic Carcinoma Cell Growth in Livers by Poly(I):Poly(C)/Cationic Liposome Complex (LIC), Oncology Research, vol. 11, pp. 497-504, 1999.
Higuchi et al., "Digestive and Absorptive Examinations by Fat and Fatty Acid Marked with Radioactive Iodine", The Kyosai Medical Journal, 1967, vol. 16, No. 1, pp. 27-32.
Office Action issued Dec. 19, 2008, in Chinese patent application No. 2005800008604.
Japanese Office Action issued Jul. 6, 2010 in Japanese patent application No. 2004-012207 (in Japanese).
James et al., "Effect of Dietary Supplementation with n-9 Eicosatrienoic Acid on Leukotriene B4 Synthesis in Rats: A Novel Approach to Inhibition of Eicosanoid Synthesis," The Journal of Experimental Medicine, vol. 178, Dec. 1993, pp. 2261-2265.
Lefkowith et al., "Manipulation of the Acute Inflammatory Response by Dietary Polyunsaturated Fatty Acid Modulation," The Journal of Immunology, vol. 145, No. 5, Sep. 1990, pp. 1523-1529.
Marone et al., "An Inhibitor of Lipoxygenase Inhibits Histamine Release from Human Basophils," Clinical Immunology and Immunopathology, vol. 17, (1980) pp. 117-122.
Jakschik et al., "Products Derived from 5.8.11-Eicosatrienoic Acid by the 5-Lipoxygenase-Leukotriene Pathway," Journal of Biological Chemistry, vol. 258, No. 21, (Nov. 1983), pp. 12797-12800.
Stenson et al., "Leukotriene B Formation by Neutrophils from Essential Fatty Acid-deficient Rats," Journal of Biological Chemistry, vol. 259, No. 19, (Oct. 1984), pp. 11784-11789.
James et al., CA 119: 225065, 1993.

* cited by examiner

*Primary Examiner* — Jason M Sims
*Assistant Examiner* — Zohreh Vakili
(74) *Attorney, Agent, or Firm* — Drinker Biddle & Reath LLP (57) ABSTRACT

To provide a preventive or ameliorating agent for liver diseases associated with hepatopathy comprising an omega-9 unsaturated fatty acid as an active ingredient.

13 Claims, 2 Drawing Sheets

PREVENTIVE OR AMELIORATING AGENT FOR LIVER DISEASE INVOLVING HEPATOPATHY

This application is the US national phase of international application PCT/JP2005/00941, filed 19 Jan. 2005, which designated the U.S. and claims priority of JP 2004-012207, dated 20 Jan. 2004, the entire contents of each of which are hereby incorporated by reference.

TECHNICAL FIELD

The present invention relates to a preventive or ameliorating agent for liver diseases associated with hepatopathy comprising, as an active ingredient, an omega-9 unsaturated fatty acid or a compound having an omega-9 unsaturated fatty acid as a constituent fatty acid, a composition or a food or drink having an effect of preventing or ameliorating liver diseases associated with hepatopathy, and a method of preparing them. More specifically it relates to a preventive or ameliorating agent for acute or chronic hepatitis, acute hepatic insufficiency, liver cirrhosis and/or hepatoma associated with hepatopathy comprising, as an active ingredient, at least one selected from the group consisting of an omega-9 unsaturated fatty acid, an alcohol ester of an omega-9 unsaturated fatty acid, a monoglyceride, a diglyceride and/or a triglyceride, or a phospholipid having an omega-9 unsaturated fatty acid as a constituent fatty acid, a composition or a food or drink having a preventing or ameliorating effect, and a method of preparing them.

BACKGROUND ART

Hepatopathy, in which the destruction of hepatic cells progresses due to viruses or various toxic substances, may be an etiologic factor that causes acute or chronic hepatitis and, furthermore, liver cirrhosis, hepatoma etc. Specifically, in acute hepatitis subjective symptoms such as nausea, vomiting and malaise are more severe than in common hepatitis, and it is known to be associated with high fever, leukocytosis, and highly positive CRP, and jaundice may abruptly aggravate, sometimes leading to premature death. Even when premature death may be avoided, an extremely large number of cases that lead to cirrhosis or hepatoma are caused by chronic hepatitis, posing a social problem.

With respect to hepatitis by etiology, viruses (type A, type B, type C, type D, type E) are a predominant cause of acute hepatitis, and type C hepatitis among them accounts for the majority of cases of chronic liver diseases in Japan, accounting for as high as 90% of the causes of hepatoma. Hepatopathy caused by an autoimmune mechanism is called autoimmune hepatic diseases, which include primary biliary cirrhosis (PBC), primary sclerosing cholangitis (PSC) and other related diseases in addition to autoimmune hepatitis.

Alcohol is primarily metabolized in the liver, and its chronic ingestion may affect various metabolic systems of the liver, causing hyperuricemia, hyperlipidemia, hyperlactemia and the like. The metabolic disorders of fatty acids may lead to the accumulation of neutral fats and the stimulation of inflammatory cells which may trigger hepatitis, and heavy drinking may lead to acute liver insufficiency, called severe alcoholic hepatitis, with a poor prognosis. The accumulation of fats in the liver cells is due to alcohol, caused by drinking, and hypernutrition, caused by obesity. Usually the accumulation of fats does not induce hepatitis, but may sometimes be associated with inflammation similar to alcoholic hepatitis, and some examples have been reported in which the disease progressed to cirrhosis.

Cirrhosis is a terminal stage of all chronic disorders of the liver and, through the repeated damage to, and regeneration of, hepatic cells, fibrosis occurs and regenerating nodules are formed throughout the entire liver. Accordingly, all hepatic diseases that exhibit chronic hepatic disorders cause the functional insufficiency of hepatic cells and portal hypertension. The etiology of about 400,000 patients with cirrhosis in Japan is predominantly virus-induced, among which hepatitis C virus accounts for 62% and hepatitis B virus for 15%. Virus-induced cirrhosis causes a high incidence of hepatoma and considerably affects the prognosis of cirrhosis as well. Other etiologies include alcohol, drugs and toxic substances, autoimmunity, cholestasis, circulatory disorders, metabolic anomalies, parasites, and the like.

As therapeutic regimens, the avoidance of causes is most important for diseases (alcohol-induced, drug-induced) for which the cause can be avoided. For virus-induced (HBV, HCV) diseases, the only therapeutic regimen available at present is interferon, but the effect is only minimal for HBV, and about 30-50% even for HCV. Recently, there were developments in which the combined use of lamivudine (antiviral agent) for type B hepatitis and ribavirin (antiviral agent) for type C hepatitis became available. On the other hand, for those cases in which viruses cannot be expelled, glucocorticoids, glycyrrhizin preparations, ursodeoxycholic acid etc. are only given for the purpose of slowing down hepatic disorders and the secondary or primary prevention of oncogenesis (Yakkyoku (The Journal of Practical Pharmacy), Vol. 54, Suppl., 2003). Thus, main therapies are ancillary liver supporting therapies, and there are no effective therapeutic agents for hepatitis or inhibitors for hepatitis induction without side effects (MEDICAL DIGEST, Vol. 39 (1), 1990).

DISCLOSURE OF THE INVENTION

Thus, there is vital need to develop a compound that prevents or ameliorates liver diseases associated with hepatopathy and that is amenable to application in foods without serious side effects.

After intensive and extensive research to resolve the above problems, the present inventors have found an omega-9 unsaturated fatty acid or a compound having an omega-9 unsaturated fatty acid as a constituent fatty acid that exhibits an excellent effect of suppressing hepatopathy, that prevents or ameliorates liver diseases associated with hepatopathy, and that is highly amenable to application as a foodstuff, and thereby have completed the present invention. Thus, the present inventors intend to provide a preventive or ameliorating agent for liver diseases associated with hepatopathy comprising as an active ingredient an omega-9 unsaturated fatty acid or a compound having an omega-9 unsaturated fatty acid as a constituent fatty acid, a composition or a food or drink having an effect of preventing or ameliorating liver diseases associated with hepatopathy, and a method of preparing them.

More specifically, the present inventors intend to provide a preventive or ameliorating agent for acute or chronic hepatitis, acute hepatic insufficiency, liver cirrhosis and/or hepatoma associated with hepatopathy comprising as an active ingredient at least one selected from the group consisting of an omega-9 unsaturated fatty acid, an alcohol ester of an omega-9 unsaturated fatty acid, a monoglyceride, a diglyceride and/or a triglyceride, or a phospholipid having an omega-9 unsaturated fatty acid as a constituent fatty acid, a composition or a food or drink having a preventing or an ameliorating effect, and a method of preparing them.

BEST MODE FOR CARRYING OUT THE INVENTION

The present invention relates to a preventive or ameliorating agent for liver diseases associated with hepatopathy comprising, as an active ingredient, an omega-9 unsaturated fatty acid or a compound having an omega-9 unsaturated fatty acid as a constituent fatty acid, a composition or a food or drink having an effect of preventing or ameliorating liver diseases associated with hepatopathy and a method of preparing them. The omega-9 unsaturated fatty acid, an active ingredient of the present invention, is a compound in which a double bond nearest to the methyl end of the fatty acid lies in between the 9th and the 10th carbon from the methyl group, and that has two or more double bonds and preferably 18-22 carbons, and include, for example, 6,9-octadecadienoic acid (18:2 ω9), 8,11-eicosadienoic acid (20:2 ω9), and 5,8,11-eicosatrienoic acid (20:3 ω9), and the like. They may be each used alone or in combination.

As naturally occurring omega-9 unsaturated fatty acids are all in the cis form, it is preferred to use omega-9 unsaturated fatty acids in the cis form in the present invention as well.

An omega-9 unsaturated fatty acid such as 5,8,11-eicosatrienoic acid (20:3 ω9, also referred to as "mead acid") and 8,11-eicosadienoic acid (20:2 ω9) are known to be present as one of the building fatty acids of the tissue of animals that have a deficiency of essential fatty acids.

These unsaturated fatty acids can be precursors of the leukotriene 3 group in vivo, and the biological activity thereof is highly promising, and "A preventing and an ameliorating agent for clinical conditions with leukotriene B4 (LTB4)" (Japanese Unexamined Patent Publication (Kokai) No. 07-041421), "A preventing and an ameliorating agent for clinical conditions via the delayed type allergic reactions" (Japanese Unexamined Patent Publication (Kokai) No. 08-053349), and "A preventive and therapeutic agent for diseases caused by the abnormal cartilage tissue" (WO97-05863) were invented, and applications to anti-inflammation, anti-allergy, anti-rheumatism and osteoarthritis have been reported. From the conventional findings, however, the effect on the liver diseases associated with hepatopathy could not have been expected, and this was clarified for the first time by evaluating in the animal models of hepatopathy of the present invention.

The active ingredient of the present invention is an omega-9 unsaturated fatty acid, and all compounds having an omega-9 unsaturated fatty acid as a constituent fatty acid can be used. Compounds having an omega-9 unsaturated fatty acid as a constituent fatty acid can be used in the form of free fatty acids, and include, for example, pharmaceutically acceptable salts of an omega-9 unsaturated fatty acid, such as sodium salts, potassium salts, lithium salts, or other alkali metal salts, zinc salts, calcium salts, magnesium salts, and the like. There can also be used lower alcohol esters of omega-9 unsaturated fatty acids, such as methyl esters of omega-9 unsaturated fatty acids, ethyl esters of omega-9 unsaturated fatty acids, and the like. There can also be used monoglycerides, diglycerides, triglycerides, phospholipids and furthermore glycolipids having omega-9 unsaturated fatty acids as building fatty acids. As used herein, the present invention is not limited to those mentioned above but all compounds having omega-9 unsaturated fatty acids as building fatty acids can be used.

Omega-9 unsaturated fatty acids or compounds having omega-9 unsaturated fatty acids as building fatty acids for use in the present invention may be from any source. Thus, they may be produced from microorganisms that can synthesize omega-9 unsaturated fatty acids or compounds having omega-9 unsaturated fatty acids as building fatty acids, animal tissues that have a deficiency of essential fatty acids or cultured animal cells that have a deficiency of essential fatty acids, or they may be chemically or enzymatically synthesized, or may be separated and purified from natural products such as animal cartilages.

When applications into foodstuffs are contemplated, omega-9 unsaturated fatty acids are preferably in the form of monoglycerides, diglycerides, triglycerides or phospholipids, and specifically triglycerides. There were no abundant sources of triglycerides containing omega-9 unsaturated fatty acids (synonymous with triglycerides in which part or all of the building fatty acids contains omega-9 unsaturated fatty acids), but the present inventors have made it possible to industrially produce triglyceride having omega-9 unsaturated fatty acids as building fatty acids, which was given to animal models of hepatopathy in order to clarify, for the first time, the effect of active ingredients of the present invention, and the effect of preventing or ameliorating liver diseases associated with hepatopathy.

As microorganisms that produce fats (triglycerides) containing omega-9 unsaturated fatty acids, there can be mentioned microorganisms having a reduced or absent Δ12 unsaturating enzyme activity that can be obtained by the mutation treatment of microorganisms belonging to genus *Mortierella*, genus *Conidiobolus*, genus *Phythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium*, or genus *Saprolegnia* and being capable of producing arachidonic acid.

Microorganisms capable of producing arachidonic acid produce stearic acid (18:0) biosynthetically from the carbon sources in the medium components, said stearic acid is converted to oleic acid (18:1 ω9) by a Δ9 unsaturating enzyme, said oleic acid is converted to linoleic acid (18:2 ω6) by a Δ12 unsaturating enzyme, said linoleic acid is converted to γ-linolenic acid (18:3 ω9) by a Δ6 unsaturating enzyme, said γ-linolenic acid is converted to dihomo-γ-linolenic acid (20:3 ω6) by a chain-elongation unsaturating enzyme, and said dihomo-γ-linolenic acid is converted to arachidonic acid (20:4 ω6) by a Δ5 unsaturating enzyme. However, when the Δ12 unsaturating enzyme is inhibited, oleic acid is changed biosynthetically to 6,9-octadecadienoic acid (18:2 ω9) by the Δ6 unsaturating enzyme, 6,9-octadecadienoic acid is changed biosynthetically to 8,11-eicosadienoic acid (20:2 ω9) by the chain-elongation unsaturating enzyme, and 8,11-eicosadienoic acid (20:2 ω9) is changed biosynthetically to 5,8,11-eicosatrienoic acid (20:3 ω9) by the Δ5 unsaturating enzyme.

Specifically, as a microorganism that can produce fats (triglycerides) containing omega-9 unsaturated fatty acids, there can be mentioned, without limit, a microorganism having the Δ5 unsaturating enzyme activity, the Δ6 unsaturating enzyme activity and a reduced or absent Δ12 unsaturating enzyme activity that can be obtained by a mutation treatment of a microorganism capable of producing arachidonic acid described in Japanese Unexamined Patent Publication (Kokai) No. 5-91888, for example *Mortierella alpina* SAM1861 (FERM BP-3590) (internationally deposited under the provisions of the Budapest Treaty on Sep. 30, 1991 with the Patent Microorganism Depository of National Institute of Industrial Science and Technology, of Chuo 6, 1-1, Higashi 1-chome, Tsukuba city, Ibaraki pref., Japan), and a microorganism having a reduced or absent Δ12 unsaturating enzyme activity and an enhanced activity of at least one of the Δ5 unsaturating enzyme activity and the Δ6 unsaturating enzyme activity and the chain elongation activity that can be obtained by a mutation treatment of a microorganism capable of producing arachidonic acid, for example *Mortierella alpina* SAM2086 (FERM BP-6032) (internationally deposited under the provisions of the Budapest Treaty on Aug. 5, 1996 with the Patent Microorganism Depository of National Institute of Industrial Science and Technology, of Chuo 6, 1-1, Higashi 1-chome, Tsukuba city, Ibaraki pref., Japan) (FERM P-15766 deposited in Japan on Aug. 5, 1996 was transferred to international deposition on Jul. 30, 1997).

In order to cultivate a microbial strain for use in the present invention, spores or mycelia of the strain or preculture obtained by pre-culturing the strain are inoculated into a liquid or on solid medium and cultured. In the case of a liquid medium, as the carbon source, there can be used, without limit, any of commonly used ones such as glucose, fructose, xylose, saccharose, maltose, soluble starch, molasse, glycerol, and mannitol.

As the nitrogen source, there can be used, in addition to natural nitrogen sources such as peptone, yeast extracts, malt extracts, meat extracts, casamino acid, corn steep liquor, soy bean protein, defatted soy bean and cotton seed grounds, organic nitrogen source such as urea, as well as inorganic nitrogen sources such as sodium nitrate, ammonium nitrate and ammonium sulfate. In addition, as needed, inorganic salts such as a phosphate, magnesium sulfate, iron sulfate and copper sulfate, and vitamins can also be used as trace nutrients. These components of the culture medium may be any concentrations as long as they do not badly affect microbial growth. Generally, for practical reasons, carbon sources and nitrogen sources may be added at the start or in the middle of culturing so that the total amount of carbon added is 0.1-40% by weight, preferably 1-25% by weight, and the total amount of nitrogen added is 0.1-20% by weight, preferably 1-10% by weight.

The culturing temperature for omega-9 unsaturated fatty acid-producing microorganisms may vary with the microorganism used and is 5-40° C., preferably 20-30° C., and also after culturing at 20-30° C. in order to increase the microbial mass, culturing may be continued at 5-20° C. to produce unsaturated fatty acids. By such a temperature control, the ratio of highly unsaturated fatty acids in the forming fatty acids can be increased. pH of the medium is 4-10, preferably 5-9, and an aerated stirring culture, a shaking culture or a stationary culture may be conducted. Culturing may generally conducted for 2-30 days, preferably for 5-20 days, and more preferably for 5-15 days.

Furthermore, as a means for enhancing the ratio of omega-9 unsaturated fatty acids in the fats (triglycerides) containing omega-9 unsaturated fatty acids, a lipid containing omega-9 unsaturated fatty acids may be subjected to selective hydrolysis to obtain a lipid containing high concentrations of omega-9 unsaturated fatty acids. A lipase for use in this selective hydrolysis has no position specificity, and the degree of hydrolysis is proportional to the number of double bonds, ester bonds of fatty acids other than the high concentrations of omega-9 unsaturated fatty acids are hydrolyzed. And an ester exchange reaction may occur between the resulting PUFA portion glycerides to yield triglycerides having enhanced unsaturated fatty acids ("Enzymatic Fractionation and Enrichment of n-9 PUFA": J. Am. Oil Chem. Soc., 80: 37-42 (2003)).

Thus, a lipid containing high concentrations of omega-9 unsaturated fatty acids obtained by selective hydrolysis of a lipid (triglyceride) containing omega-9 unsaturated fatty acids may be used as an active ingredient of the present invention. The ratio of omega-9 unsaturated fatty acids relative to the total fatty acids of the lipid (triglyceride) containing omega-9 unsaturated fatty acids of the present invention, specifically an omega-9 unsaturated fatty acid comprising at least one selected from the group consisting of 6,9-octadecadienoic acid (18:2 ω9), 8,11-eicosadienoic acid (20:2 ω9) and 5,8,11-eicosatrienoic acid (20:3 ω9) is preferred to be high for the purpose of eliminating the effect of other fatty acids.

However, the present invention is not limited to high ratios, but in practice, the absolute amount of omega-9 unsaturated fatty acids may sometimes count when application into foodstuffs is to be contemplated, and a lipid (triglyceride) containing 20% by weight or more, preferably 30% by weight or more, and more preferably 40% by weight or more of omega-9 unsaturated fatty acid can substantially be used. Furthermore, a lipid (triglyceride) containing 10% by weight or more, preferably 20% by weight or more, and more preferably 30% by weight or more of 5,8,11-eicosatrienoic acid (20:3 ω9) can, substantially, be used.

A lipid containing omega-9 unsaturated fatty acids may be obtained from the cultured cell mass of a microorganism capable of producing omega-9 unsaturated fatty acids by destructing the cell mass, drying as needed, and by subjecting to an extraction treatment with an organic solvent such as n-hexane or with supercritical carbon dioxide gas. Also, by subjecting said lipid to hydrolysis or esterification, a mixture of free fatty acids containing omega-9 unsaturated fatty acids or fatty acid ester mixture can be obtained. Furthermore, said mixture of free fatty acids or fatty acid ester mixture may be subjected to a standard urea fractionation method, liquid-liquid chromatography, column chromatography, etc. to obtain free fatty acids or fatty acid esters of 6,9-octadecadienoic acid, 8,11-eicosadienoic acid and 5,8,11-eicosatrienoic acid at a purity of 80% or higher.

An omega-9 unsaturated fatty acid which is the active ingredient of the present invention is not always limited to a highly purified product, but a compound having an omega-9 unsaturated fatty acid as a constituent fatty acid, specifically a triglyceride, a diglyceride, a monoglyceride, a phospholipid, and a glycolipid containing an omega-9 unsaturated fatty acid can be used. Furthermore, said compound having an omega-9 unsaturated fatty acid as a constituent fatty acid can be used alone or in combination with a free fatty acid mixture containing an omega-9 unsaturated fatty acid or a fatty acid ester mixture.

The present invention relates to a preventive or ameliorating agent for liver diseases associated with hepatopathy comprising as an active ingredient an omega-9 unsaturated fatty acid or a compound having an omega-9 unsaturated fatty acid as a constituent fatty acid, a composition or a food or drink having an effect of preventing or ameliorating liver diseases associated with hepatopathy and a method of preparing them, and liver diseases associated with hepatopathy which are the subject of the present invention include, for example, acute or chronic hepatitis caused by viral hepatitis, drug-induced hepatitis, alcohol-induced hepatitis or fat-induced hepatitis, and as diseases estimated to occur after the progression of these hepatitis there can be mentioned acute hepatic insufficiency, liver cirrhosis and hepatoma.

In the production of a food or drink having an effect of preventing or ameliorating liver diseases associated with hepatopathy, an omega-9 unsaturated fatty acid and a compound having an omega-9 unsaturated fatty acid as a constituent fatty acid may be used alone or may be blended with a material for a food or drink that substantially contains no or little, if any, omega-9 unsaturated fatty acids.

In the case of a triglyceride in which part or all of the building fatty acids contains omega-9 unsaturated fatty acids, lipids (triglycerides) have numerous potential in its application, and can be used as raw materials or additives for foods, beverages, cosmetics, and pharmaceuticals. The intended use and the amount used has no limitation.

For example, as food compositions there can be mentioned functional foods, nutrient supplements, modified milk for premature infants, modified milk for babies, baby foods, foods for pregnant women or foods for the aged people, and the like. Also under the control of a dietician based on a doctor's prescription, an omega-9 unsaturated fatty acid and/or a compound having an omega-9 unsaturated fatty acid as a constituent fatty acid may be added to any food at the cooking of hospital diet, and can be given to patients in the form of a cooked food on site.

As examples of foods containing lipids, there can be mentioned natural foods that originally contain lipids such as meat, fish and nuts, foods to which lipids are added at the time of cooking such as soup, foods for which lipids are used as a heat medium for donuts etc., fatty foods such as butter, processed foods to which fats are added at the time of processing cockeys etc., or foods to which fats are sprayed or applied at the end of processing such as hard biscuits, and the like. Furthermore, fats may be added to agricultural foods, fermented foods, livestock food products, aquatic foods, or beverages that contain no lipids. Furthermore, they may be in the form of functional foods or pharmaceuticals, and may also be processed form such as enteral foods, powders, granules, troches, oral liquids, suspensions, emulsions, syrups and the like.

The composition of the present invention may contain various carriers and additives that are generally used for a food or drink, pharmaceuticals or quasi drugs in addition to the active ingredient of the present invention. Specifically it is preferred to contain antioxidants in order to prevent oxidation of the active ingredient of the present invention. As antioxidants, there can be mentioned naturally occurring antioxidants such as tocopherols, flavone derivatives, phyllodulcins, kojic acid, gallic acid, catechins, fuki acid, gossypol, pyrazine derivatives, sasamol, guaiacol, guaiac acid, p-coumaric acid, nordihydroguaiatic acid, sterols, terpenes, nucleobases, carotenoids and lignins, and synthetic antioxidants represented by ascorbate-palmitate ester, ascorbate-stearate ester, butyl hydroxy anisole (BHA), butyl hydroxy toluene (BHT), mono-t-butyl hydroxy quinone (TBHQ), and 4-hydroxymethyl-2,6-di-t-butyl phenol (HMBP).

In tocopherols, α-tochopherol, β-tocopherol, γ-tocopherol, Δ-tocopherol, ε-tocopherol, ξ-tocopherol, η-tocopherol, and tocopherol esters (tocopherol acetates etc.) may be mentioned as related compounds. In carotenoids, there can be mentioned, for example, β-carotene, canthaxantin, astaxanthin and the like.

As carriers the composition of the present invention can include, in addition to the active ingredient of the present invention, various carriers, extender agents, diluents, bulking agents, dispersants, excipients, binding solvents (for example water, ethanol, vegetable oils), solubilizing agents, buffers, dissolution-promoting agents, gelling agents, suspending agents, wheat flour, rice flour, starch, corn starch, polysaccharides, milk proteins, collagen, rice oils, lecithin and the like. As additives, it can include, without limit, vitamins, sweeteners, coloring agents, perfumes, anti-wetting agents, fibers, electrolytes, minerals, nutrients, antioxidants, preservatives, flavoring agents, wetting agents, extracts of natural foods, vegetable extracts and the like.

When the active ingredient of the present invention is actually applied to a food or drink, the absolute amount of an omega-9 unsaturated fatty acid that is blended with the food is important. However, when a triglyceride containing a triglyceride in which part or all of the building fatty acids is the omega-9 unsaturated fatty acids is added to a food, it is blended to 0.001% by weight or more, preferably 0.01% by weight or more, more preferably 0.1% by weight or more as the omega-9 unsaturated fatty acids, as the absolute amount to be blended to a food or drink may vary with the amount ingested of the blended food or a drink. Furthermore, it is added to 0.0003% by weight or more, preferably 0.003% by weight or more, more preferably 0.03% by weight or more as the 5,8,11-eicosatrienoic acid, and can be processed and produced by a conventional method.

A food or drink containing the fatty acids of the present invention can be orally taken, for the purpose of preventing or ameliorating diseases associated with hepatopathy and of maintaining health, roughly in the range of 0.001 g-10 g, preferably 0.001 g-5 g, and more preferably 0.001 g-2 g of the fatty acid of the present invention per day.

When the composition of the present invention is used as a pharmaceutical product, it can be produced according to a method commonly used in the field of pharmacy and, for example, by a method described in the Japanese Pharmacopoeia or a method in conformity therewith.

When the composition of the present invention is used as a pharmaceutical product, the amount blended of the active ingredient in the composition is not specifically limited and can be used at a suitable blend ratio, as appropriate, as long as the purpose of the present invention is attained.

When the composition of the present invention is used as a pharmaceutical product, the dosage form may be any form as long as the oral or parenteral administration can be conveniently performed, and there can be mentioned injections, infusions, powders, granules, tablets, capsules, enteric coated tablets, troaches, peroral liquid preparations, suspensions, emulsions, syrups, liquids for external use, medicines for stupe, nasal drops, eye drops, inhalants, ointments, lotions, suppositories, and the like, which may be used according to disease conditions, and specifically oral administration is preferred. These pharmaceutical preparations may be formulated according to standard methods by adding to the active ingredient known adjuvants commonly used in the field of pharmacy such as additives, antioxidants, excipients, binders, disintegrants, lubricants, and flavoring agents.

Dosage of the composition of the present invention may differ with age, body weight, disease condition, administration frequency etc., and the daily dosage of an omega-9 unsaturated fatty acid and/or a compound having an omega-9 unsaturated fatty acid as a constituent fatty acid of the present invention, in terms of omega-9 unsaturated fatty acid, for an adult (about 60 kg) is generally about 0.001 g-20 g, preferably 0.01 g-10 g, more preferably 0.05 g-5 g, and most preferably 0.1 g-2 g which may be daily administered in 1-3 divided doses. Furthermore, in terms of 5,8,11-eicosatrienoic acid, it may be administered generally about 0.0001 g-10 g, preferably 0.001 g-5 g, more preferably 0.01-2 g, and most preferably 0.05 g-2 g which may be daily administered in 1-3 divided doses.

Fatty acids that are active ingredients of the present invention are known to be biological components that are formed biosynthetically, and when they are administered to 7 week-old ICR male mice at 2 g/Kg/day for two consecutive weeks (oral), no abnormal symptoms were observed, indicating that they are excellent in terms of safety.

EXAMPLES

The present invention will now be explained, in more detail, with reference to specific examples. It should be noted, however, that the present invention is not limited by these examples in any way.

Reference Example 1

A Preparation Method of a Triglyceride Having an omega-9 unsaturated fatty acid as a constituent fatty acid Five liters of a medium (pH 6.0) containing 4% glucose and 1% yeast extracts was fed into a 10 L jar fermentor and sterilized at 120° C. for 30 minutes. 100 ml of a preculture of *Mortierella alpina* mutant strain SAM1861 or SAM2086 was inoculated, and was subjected to an aerated stirring culture at an aeration of 1 vvm, a stirring speed of 300 rpm for eight days. The culture temperature was 28° C. at the start of culturing, and decreased to 20° C. from day 2. From day 1 to day 4, 1% glucose was added daily.

After the completion of culturing, filtration and drying was conducted to obtain a cell mass having an omega-9 unsaturated fatty acid as a constituent fatty acid, and by hexane extraction of the cell mass obtained, lipids were obtained, and via a purification process (degumming, deacidification, deodorization, depigmentation), an omega-9 unsaturated fatty acid-containing triglyceride (the omega-9 unsaturated fatty acid is bound at an arbitrary position of the triglyceride) was obtained.

The lipid (triglyceride) obtained was methylesterified, and the fatty acid methyl ester obtained was analyzed by gas chromatography, which indicated that when the SAMP1861 strain was cultured, the ratio of 6,9-octadecadienoic acid (18:2 ω9), 8,11-eicosadienoic acid (20:2 ω9) and 5,8,11-eicosatrienoic acid (20:3 ω9) relative to the total fatty acids was 12.94%, 3.29% and 16.83%, respectively, and when the SAMP2086 strain was cultured, the ratio of 6,9-octadecadienoic acid (18:2 ω9), 8,11-eicosadienoic acid (20:2 ω9) and 5,8,11-eicosatrienoic acid (20:3 ω9) relative to the total fatty acids was 12.41%, 3.58% and 20.87%, respectively.

Furthermore, the above omega-9 unsaturated fatty acid-containing lipid (triglyceride) was ethylesterified, and by the standard high performance liquid chromatography of the fatty acid ethyl ester mixture, a 98% pure 5,8,11-eicosatrienoic acid ethyl ester was separated and purified.

Example 1

Figure 1:
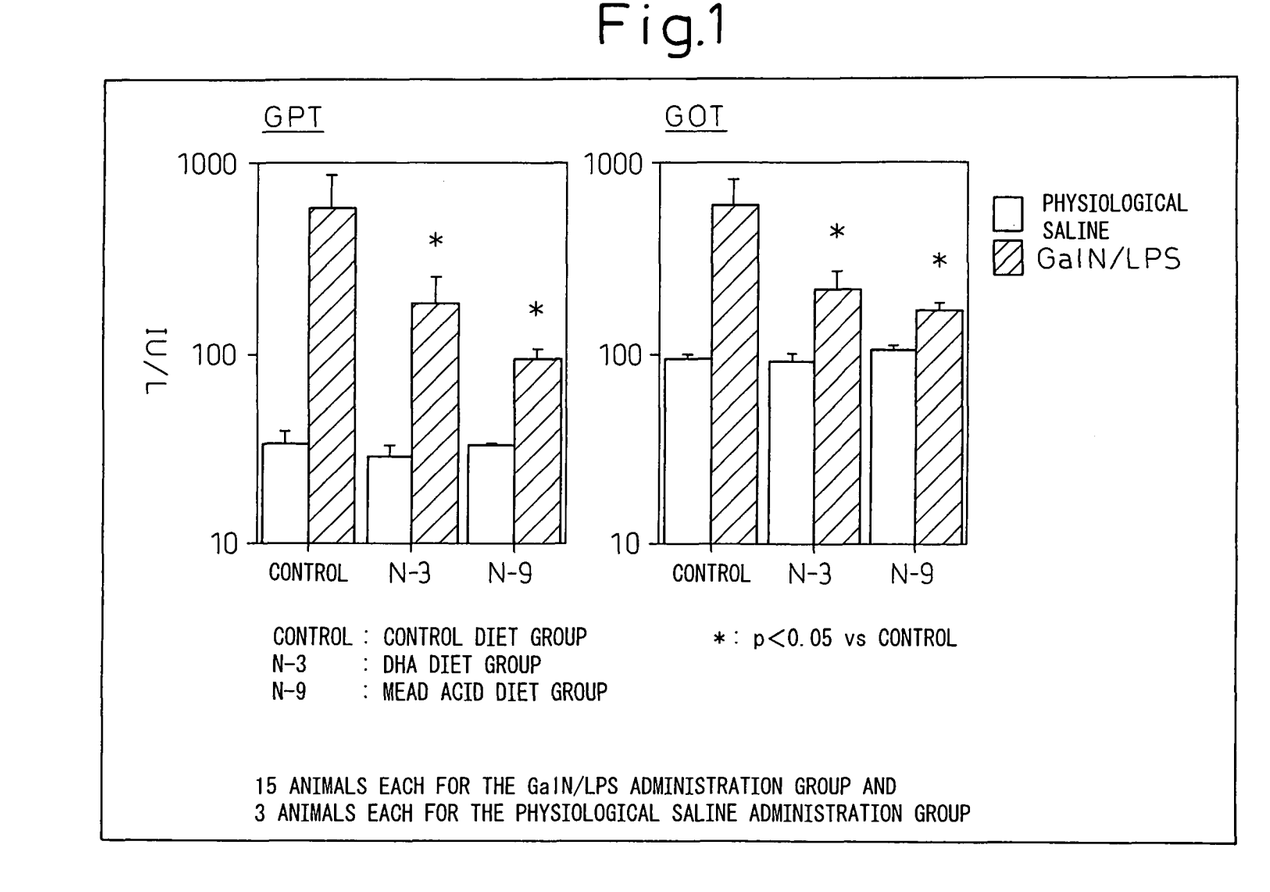
FIG. 1 is a graph showing an effect of mead acid on hepatic function markers in hepatopathy induced by galactosamine. In the figure, control indicates the control diet group, N-3 indicates the DHA diet group, and N-9 indicates the mead acid diet group. Fifteen mice were used for each of the GalN/ LPS administration group and three mice were used for each of the physiological saline administration group.

Evaluation 1 of the omega-9 unsaturated fatty acid-containing lipid in an Animal Model of Hepatopathy Four-week-old male ddY mice were given a commercially available feed to which 8% of palm oil (control diet), 8% of a lipid SUNTGM17 having 6,9-octadecadienoic acid (18:2 ω9), 8,11-eicosadienoic acid (20:2 ω9) and 5,8,11-eicosatrienoic acid (20:3 ω9) prepared in Reference Example 1 at 12.94%, 3.29% and 16.83%, respectively, as building fatty acids (mead acid diet), and a mixture of 5% fish oil containing 22% DHA and 3% triolein (DHA diet) for three weeks, and then they were intraperitoneally given physiological saline in which D-galactosamine and lipopolysaccharide were dissolved to 800 mg/kg and 25 μg/kg and mixed (GalN/LPS). Blood was drawn six hours after the GalN/LPS administration, serum was separated, and GPT and GOT activities in the serum were determined, which confirmed that GalN/LPS administration induced hepatopathy and increases in GPT and GOT activities, but it was significantly lower in the mead acid diet group than in the control diet group and the DHA diet group, indicating that mead acid clearly suppresses hepatopathy and the suppressive effect is more potent than DHA (FIG. 1).

Example 2

Figure 2:
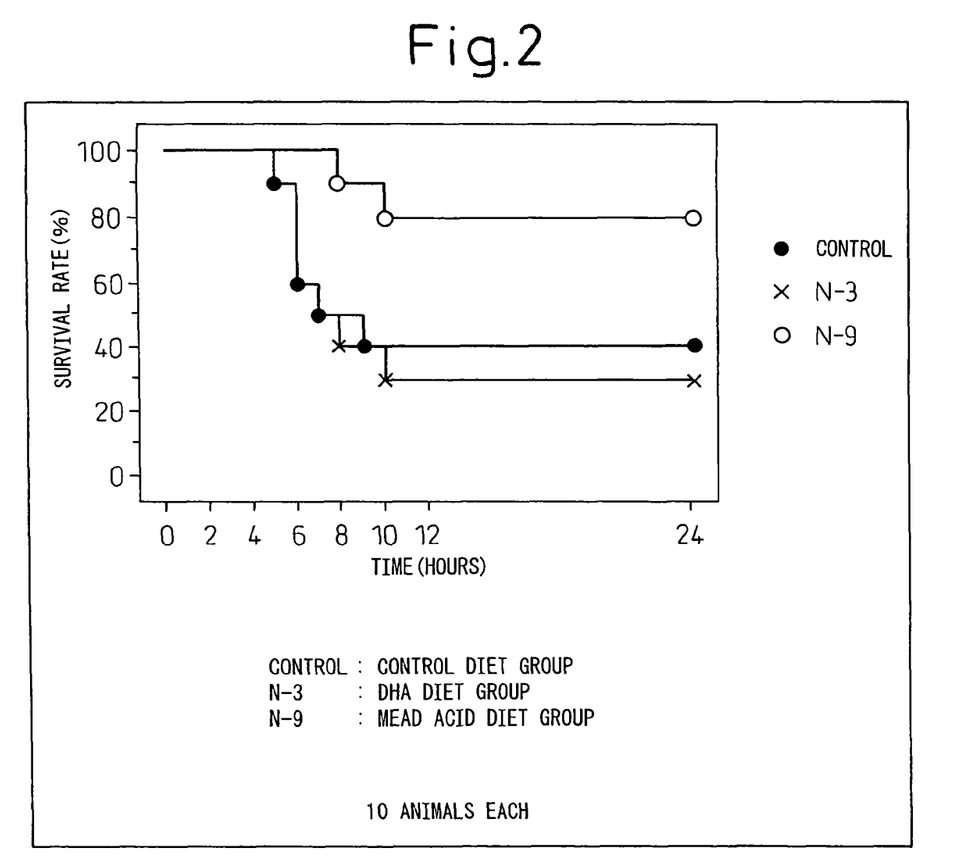
FIG. 2 is a graph showing an effect of mead acid on survival in hepatopathy induced by galactosamine. In the figure, control indicates the control diet group, N-3 indicates the DHA diet group, and N-9 indicates the mead acid diet group. Ten mice were used for each group.

Evaluation 2 of the omega-9 unsaturated fatty acid-containing Lipid in an Animal Model of Hepatopathy Four-week-old male ddY mice were given a commercially available feed to which 8% of palm oil (control diet), 8% of SUNTGM17 similar to Example 1 (mead acid diet), and a mixture of 5% fish oil containing 22% DHA and 3% triolein (DHA diet) for three weeks, and then they were intraperitoneally given physiological saline in which D-galactosamine and lipopolysaccharide were dissolved to 800 mg/kg and 75 μg/kg and mixed (GalN/LPS). After the GalN/LPS administration, the number of surviving animals was counted every hour until 24 hours later, and the survival rate was calculated, which indicated that the survival rate in the mead acid diet group was significantly higher than in the control group and the DHA diet group (FIG. 2).

Example 3

Evaluation of 5,8,11-eicosatrienoic acid ethyl ester in an Animal Model of Hepatopathy Four-week-old male ddY mice were orally given 10 mg/kg of 5,8,11-eicosatrienoic acid ethyl ester (mead acid) purified from the lipid SUNTGM17 prepared in Reference Example 1 for one week, and then they were intraperitoneally given physiological saline in which D-galactosamine and lipopolysaccharide were dissolved to 800 mg/kg and 25 μg/kg and mixed (GalN/LPS). Six hours after the GalN/LPS administration, blood was drawn, serum was separated, and GPT and GOT activities in the serum were determined, which confirmed that the GOT activity was 1024±94 IU/L in the control diet group, whereas it was 413±37 IU/L in the mead acid diet group, indicating a significant suppression of hepatopathy.

Example 4

Capsule Preparation

To 100 parts by weight of gelatin and 35 parts by weight of food additive glycerin, water was added and dissolved at 50-60° C. to prepare a gelatin coat with a viscosity of 2000 cp. Then vitamin E oil was mixed to 0.05% by weight in a lipid (triglyceride) having an omega-9 unsaturated fatty acid as a constituent fatty acid prepared in Reference Example 1 to prepare a content 1. Then, to 98% 5,8,11-eicosatrienoic acid ethyl ester obtained in Reference Example 1, vitamin E oil was mixed to 0.05% by weight to prepare a content 2. Using these contents 1 and 2, capsule molding and drying was performed according to a standard method to produce soft capsules containing 200 mg of the content per granule.

Example 5

Use in a Fat Infusion

Four hundred grams of a lipid (triglyceride) having an omega-9 unsaturated fatty acid as a constituent fatty acid obtained in Reference Example 1, 48 g of purified egg yolk lecithin, 20 g of oleic acid, 100 g of glycerin and 40 ml of 0.1N caustic soda were added, and dispersed with a homogenizer, to which distilled water for injection was added to make up to 4 liters. This was emulsified with a high-pressure spray emulsifier to prepare a lipid emulsion. Said lipid emulsion was dispensed in a plastic bag in 200 ml aliquots, and then subjected to high-pressure steam sterilization at 121° C. for 20 minutes to prepare a fat infusion.

Example 6

Use in a Juice

Two grams of β-cyclodextrin was added to 20 ml of a 20% aqueous ethanol, to which 100 mg of a lipid (triglyceride) (vitamin E has been added to 0.05% by weight) having an omega-9 unsaturated fatty acid as a constituent fatty acid prepared in Reference Example 1 was added under stirring, and incubated at 50° C. for two hours. After cooling (for about one hour) to room temperature, stirring was continued to incubate at 4° C. for 10 hours. The precipitate formed was recovered by centrifugation, washed in n-hexane, lyophilized to obtain 1.8 g of a cyclodextrin inclusion compound containing a lipid (triglyceride) having an omega-9 unsaturated fatty acid as a constituent fatty acid. One gram of this powder was homogeneously mixed with 10 L of a juice to prepare a juice containing a lipid (triglyceride) having an omega-9 unsaturated fatty acid as a constituent fatty acid.

What is claimed is:

1. A method of ameliorating liver diseases associated with hepatopathy comprising administering an omega-9 unsaturated fatty acid or a compound having an omega-9 unsaturated fatty acid as a constituent fatty acid as an active component to a subject to ameliorate liver diseases associated with hepatopathy, wherein the subject administers the omega-9 unsaturated fatty acid in an amount of (1) 0.001-10 g per day, or (2) 0.001-20 g per 60 kg body weight in 1-3 divided doses daily, wherein the subject is a patient having a liver disease associated with hepatopathy, and wherein the liver diseases associated with hepatopathy are acute hepatic insufficiency, liver cirrhosis and/or hepatoma.

2. The method according to claim 1 wherein said compound having an omega-9 unsaturated fatty acid as a constituent fatty acid is an alcohol ester of an omega-9 unsaturated fatty acid, a monoglyceride, a diglyceride and/or a triglyceride, or a phospholipid having an omega-9 unsaturated fatty acid as a constituent fatty acid.

3. The method according to claim 2 wherein said triglyceride having an omega-9 unsaturated fatty acid as a constituent fatty acid contains 20% or more of the omega-9 unsaturated fatty acid relative to the total fatty acids constituting said triglyceride.

4. The method according to claim 1 wherein said omega-9 unsaturated fatty acid is at least one selected from the group consisting of 6,9-octadecadienoic acid (18:2 ω9), 8,11-eicosadienoic acid (20:2 ω9) and 5,8,11-eicosatrienoic acid (20:3 ω9).

5. The method according to claim 1 wherein said triglyceride having an omega-9 unsaturated fatty acid as a constituent fatty acid is obtained by culturing a microorganism having a reduced or absent Δ12 unsaturating enzyme activity in a medium, said microorganism being obtained by the mutation treatment of a microorganism belonging to genus *Mortierella*, genus *Conidiobolus*, genus *Phythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium*, or genus *Saprolegnia* and being capable of producing arachidonic acid, and then extracting from said culture.

6. A method of ameliorating liver diseases associated with hepatopathy comprising providing a composition or a food or drink containing an omega-9 unsaturated fatty acid or a compound having an omega-9 unsaturated fatty acid as a constituent fatty acid as an active component to a subject to ameliorate liver diseases associated with hepatopathy, wherein the subject is a patient having a liver disease associated with hepatopathy, and wherein the liver diseases associated with hepatopathy are acute hepatic insufficiency, liver cirrhosis and/or hepatoma.

7. The method according to claim 6 wherein said compound having an omega-9 unsaturated fatty acid as a constituent fatty acid is an alcohol ester of an omega-9 unsaturated fatty acid, a monoglyceride, a diglyceride and/or a triglyceride, or a phospholipid having an omega-9 unsaturated fatty acid as a constituent fatty acid.

8. The method according to claim 7 wherein said triglyceride having an omega-9 unsaturated fatty acid as a constituent fatty acid contains 20% or more of the omega-9 unsaturated fatty acid relative to the total fatty acids constituting said triglyceride.

9. The method according to claim 6 wherein said omega-9 unsaturated fatty acid is at least one selected from the group consisting of 6,9-octadecadienoic acid (18:2 ω9), 8,11-eicosadienoic acid (20:2 ω9) and 5,8,11-eicosatrienoic acid (20:3 ω9).

10. The method according to claim 7 wherein said triglyceride having an omega-9 unsaturated fatty acid as a constituent fatty acid is obtained by culturing a microorganism having a reduced or absent Δ12 unsaturating enzyme activity in a medium, said microorganism being obtained by the mutation treatment of a microorganism belonging to genus *Mortierella*, genus *Conidiobolus*, genus *Phythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium*, or genus

*Saprolegnia* and being capable of producing arachidonic acid, and then extracting it from said culture.

11. The method according to claim 6 wherein said food or drink are functional foods, nutrient supplements, specified health foods or foods for old people.

12. The method of claim 1, wherein the subject is administered the omega-9 unsaturated fatty acid in an amount of 0.001-2 g per day.

13. The method of claim 1, wherein the subject is administered the omega-9 unsaturated fatty acid in an amount of 0.1-2 g per 60 kg body weight in 1-3 divided doses daily.

* * * * *

UNITED STATES PATENT AND TRADEMARK OFFICE
CERTIFICATE OF CORRECTION

PATENT NO. : 8,436,047 B2  
APPLICATION NO. : 10/562716  
DATED : May 7, 2013  
INVENTOR(S) : Ishikura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1274 days.

Signed and Sealed this
Eighth Day of September, 2015

Michelle K. Lee
*Director of the United States Patent and Trademark Office*